United States Patent
Hwang et al.

(10) Patent No.: US 8,883,951 B2
(45) Date of Patent: Nov. 11, 2014

(54) COMPOSITION COMPRISING A MONOMER FOR POLYMERIZING BRANCH-TYPE SILSESQUIOXANE POLYMER, BRANCH-TYPE SILSESQUIOXANE POLYMER SYNTHESIZED FROM THE SAME AND A METHOD FOR SYNTHESIZING THE SAME

(75) Inventors: Seung Sang Hwang, Seoul (KR); Kyung Youl Baek, Seoul (KR); He Seung Lee, Seoul (KR); Soon Man Hong, Seoul (KR); Soon Jong Kwak, Seoul (KR); Chong Min Koo, Gyeonggi-do (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 13/820,298

(22) PCT Filed: Sep. 16, 2011

(86) PCT No.: PCT/KR2011/006864
§ 371 (c)(1),
(2), (4) Date: Mar. 1, 2013

(87) PCT Pub. No.: WO2012/036510
PCT Pub. Date: Mar. 22, 2012

(65) Prior Publication Data
US 2013/0165617 A1    Jun. 27, 2013

(30) Foreign Application Priority Data
Sep. 17, 2010  (KR) .......................... 10-2010-0091767

(51) Int. Cl.
C08G 77/04  (2006.01)
C08L 83/04  (2006.01)
C07F 7/21   (2006.01)
C08G 77/16  (2006.01)

(52) U.S. Cl.
CPC ................ $C08G$ 77/04 (2013.01); $C08G$ 77/16 (2013.01); $C08L$ 83/04 (2013.01); $C08G$ 77/045 (2013.01); $C07F$ 7/21 (2013.01)
USPC .............................................. 528/20; 528/37

(58) Field of Classification Search
None
See application file for complete search history.

(56) References Cited

U.S. PATENT DOCUMENTS 3,954,823 A * 5/1976 Frye et al. ..................... 556/460
4,399,266 A   8/1983 Matsumura et al.
(Continued)

FOREIGN PATENT DOCUMENTS

KR   1020050005759 A   1/2005
KR   1020060090478 A   8/2006
(Continued)

OTHER PUBLICATIONS

John F. Brown, Jr. "The Polycondensation of Phenylsilanetriol" J. Am. Chem. Soc. 87(19), 1965, 4317-4324.*
(Continued)

Primary Examiner — Robert S Loewe
(74) Attorney, Agent, or Firm — Ladas & Parry LLP

(57) ABSTRACT

A monomer composition for polymerizing a branch-type silsesquioxane polymer is disclosed. The monomer composition includes hydroxy-substituted cyclic siloxane in a solvent, and the hydroxy-substituted cyclic siloxane includes stereoisomers of cyclic siloxane of cis, trans, random and twist structures at controlled ratios. Also disclosed are a branch-type silsesquioxane polymer synthesized by polymerizing the monomer composition for polymerizing a branch-type silsesquioxane polymer, and a method for synthesizing the same. In accordance with the disclosure, the isomers can be isolated stably at desired ratios. The isolated isomers may be polymerized into polymers of various types. Since the polymers exhibit low dielectric property, they may be utilized as low dielectric materials.

14 Claims, 16 Drawing Sheets

(56) References Cited

U.S. PATENT DOCUMENTS

| | | | |
|---|---|---|---|
| 4,999,397 | A | 3/1991 | Weiss et al. |
| 6,231,989 | B1 | 5/2001 | Chung et al. |
| 6,774,202 | B2 * | 8/2004 | Lee .................................. 528/33 |
| 7,279,434 | B2 * | 10/2007 | Hata et al. ...................... 438/778 |
| 7,423,166 | B2 | 9/2008 | Chen et al. |
| 2005/0287818 | A1 | 12/2005 | Hata et al. |
| 2006/0115658 | A1 * | 6/2006 | Mah et al. ...................... 428/447 |
| 2006/0159938 | A1 | 7/2006 | Lee et al. |
| 2006/0175683 | A1 | 8/2006 | Shin et al. |
| 2007/0238317 | A1 | 10/2007 | Allen et al. |
| 2009/0269942 | A1 | 10/2009 | Shin et al. |

FOREIGN PATENT DOCUMENTS

| | | |
|---|---|---|
| KR | 1020100131347 A | 12/2010 |
| WO | 01/46295 A1 | 6/2001 |

OTHER PUBLICATIONS

Makarova et al. "Synthesis of new stereoregular 2,4,6,8-tetraphenylcyclotetrasiloxanes with mesogenic groups and the influence of spatial isomerism on the phase state of individual isomers and their mixtures", Russ. Chem. Bull. Int. Ed. 53(9), 2004, 1983-1992.*

Unno et al. "Stereoisomers of 1,3,5,7-Tetrahydroxy-1,3,5,7-tetraisopropylcyclotetrasiloxane: Synthesis and Structures in the Crystal" J. Am. Chem. Soc. 2005, 127, 2256-2263.*

Seki et al. "Synthesis and structure of ladder polymethylsilsesquioxanes from sila-functional cyclotetrasiloxanes", J. Organomet. Chem. 695, 2010, 1363-1369.*

International Search Report; mailed Apr. 27, 2012; PCT/KR2011/006864.

* cited by examiner

COMPOSITION COMPRISING A MONOMER FOR POLYMERIZING BRANCH-TYPE SILSESQUIOXANE POLYMER, BRANCH-TYPE SILSESQUIOXANE POLYMER SYNTHESIZED FROM THE SAME AND A METHOD FOR SYNTHESIZING THE SAME

TECHNICAL FIELD

The present disclosure relates to a monomer composition for polymerizing a branch-type silsesquioxane polymer including stereoisomers of hydroxy-substituted cyclic siloxane, a branch-type silsesquioxane polymer synthesized from the same, and a method for synthesizing the same.

BACKGROUND ART

As interests in silicon-based polymers is increasing, ladder-type polymer silicon materials are drawing attentions due to their ability to supplement the shortcomings of the useful single-bonded linear siloxanes. The use of the ladder-type silicon polymers is increasing rapidly because of their structural stability and good thermal stability and compatibility with organic solvents.

A hydroxy-substituted cyclic siloxane monomer has four structural isomers of cis, trans, random and twist structures. The existing method of isolating each structural isomer, for example by HPLC or recrystallization, requires long time and has low yield.

DISCLOSURE OF INVENTION

Technical Problem

This disclosure is directed to providing branch-type silsesquioxane polymers of various structures by isolating isomers easily, quickly and without deformation of materials at desired ratios, and using a monomer composition for polymerizing a branch-type silsesquioxane polymer including the isomers at desired ratios.

The disclosure is also directed to providing a branch-type silsesquioxane polymer exhibiting effective properties by controlling the degree of branching through the ratio of the isomers during polymerization, and a method for synthesizing the same.

Solution to Problem

In one general aspect, there is provided a monomer composition for polymerizing a branch-type silsesquioxane polymer, including hydroxy-substituted cyclic siloxane in a solvent, wherein the hydroxy-substituted cyclic siloxane includes stereoisomers of cyclic siloxane of cis, trans, random and twist structures at controlled ratios.

In another general aspect, there is provided a branch-type silsesquioxane polymer synthesized from polymerization of the monomer composition for polymerizing a branch-type silsesquioxane polymer.

In another general aspect, there is provided a method for synthesizing the branch-type silsesquioxane polymer, including: controlling the ratios of cis, trans, random and twist stereoisomers of hydroxy-substituted cyclic siloxane; and polymerizing the hydroxy-substituted cyclic siloxane with the cis, trans, random and twist stereoisomers at the controlled ratios as monomer in a solvent in the presence of a catalyst.

In another general aspect, there is provided a low dielectric material comprising the branch-type silsesquioxane polymer.

Advantageous Effects of Invention

Because of very high reactivity, hydroxy-substituted cyclic siloxane exhibits poor thermal stability and gelation occurs when it is obtained as solid using a general nonpolar solvent according to the existing method, making it difficult to obtain isomers of the hydroxy-substituted cyclic siloxane. The present disclosure allows isolation of isomers stably and at desired ratios and polymerization of the isolated isomers into various polymer types.

BRIEF DESCRIPTION OF DRAWINGS

The above and other aspects, features and advantages of the disclosed exemplary embodiments will be more apparent from the following detailed description taken in conjunction with the accompanying drawings in which.

MODE FOR THE INVENTION

Exemplary embodiments now will be described more fully hereinafter with reference to the accompanying drawings, in which exemplary embodiments are shown. This disclosure may, however, be embodied in many different forms and should not be construed as limited to the exemplary embodiments set forth therein. Rather, these exemplary embodiments are provided so that this disclosure will be thorough and complete, and will fully convey the scope of this disclosure to those skilled in the art. In the description, details of well-known features and techniques may be omitted to avoid unnecessarily obscuring the presented embodiments.

The terminology used herein is for the purpose of describing particular embodiments only and is not intended to be limiting of this disclosure. As used herein, the singular forms a, an and the are intended to include the plural forms as well, unless the context clearly indicates otherwise. Furthermore, the use of the terms a, an, etc. does not denote a limitation of quantity, but rather denotes the presence of at least one of the referenced item. The use of the terms first, second, and the like does not imply any particular order, but they are included to identify individual elements. Moreover, the use of the terms first, second, etc. does not denote any order or importance, but rather the terms first, second, etc. are used to distinguish one element from another. It will be further understood that the terms comprises and/or comprising, or includes and/or including when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Figure 1:
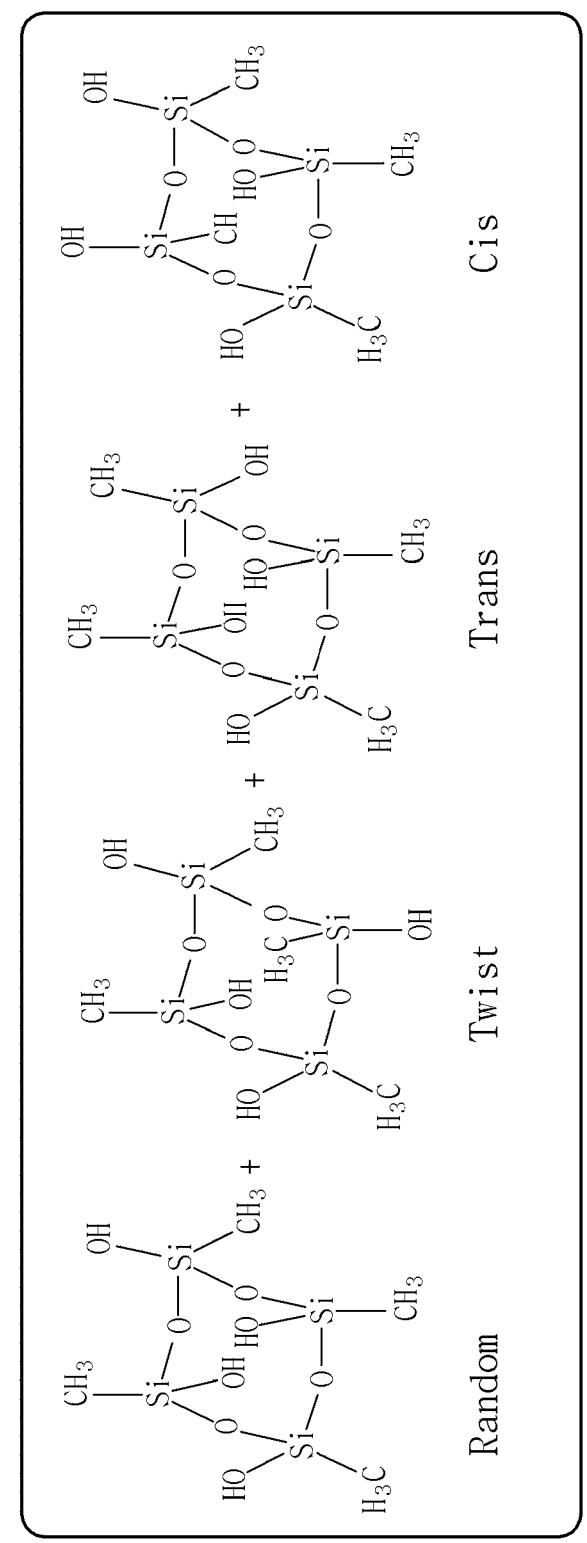
FIG. 1 shows four structural isomers of 2,4,6,8-tetrahydroxytetramethylcyclosiloxane.

The monomer composition according to the present disclosure comprises hydroxy-substituted cyclic siloxane in a solvent. The hydroxy-substituted cyclic siloxane comprises stereoisomers of cyclic siloxane of cis, trans, random and twist structures at controlled ratios. The structures of the stereoisomers are illustrated in FIG. 1.

Since the method of isolating the four isomers separately gives low yield, in the present disclosure, a monomer composition comprising the stereoisomers of cyclic siloxane of cis, trans, random and twist structures at controlled ratios is used to prepare a desired branch-type silsesquioxane polymer.

In an embodiment, polymers of different types may be polymerized depending on the ratio of the trans stereoisomer in the stereoisomers. The ratio of the trans stereoisomer is not particularly limited as long as the branch-type silsesquioxane polymer can be polymerized. The ratio of the trans stereoisomer may be, for example, 15-95%, specifically 20-90%, more specifically 30-85%, further more specifically 35-85%. If the ratio of the trans stereoisomer is lower, modulus may decrease. And, if it is too high, the resulting polymer may be brittle.

The solvent may be one which does not gelate by reacting with the stereoisomers and has such a superior solubility as to allow effective isolation of the isomers. The solvent may be, for example, one or more selected from a group consisting of toluene, hexane, methylene chloride, chloroform, tetrahydrofuran (THF), cyclohexane and a mixture thereof. Specifically, it may be a mixture solvent of THF and cyclohexane. The solvent including cyclohexane stably recrystallizes the monomers so that the desired isomers can be isolated, whereas the solvent including toluene, hexane, methylene chloride or chloroform may not allow effective isolation of the isomers due to gelation.

In the mixture solvent, e.g., in the mixture solvent comprising THF and cyclohexane, a higher proportion of THF results in predominant trans isomer but may lead to decreased yield. Thus, the ratio of THF and cyclohexane may be determined in consideration thereof. The ratio of THF and cyclohexane in the mixture solvent may be, for example, 1:1 to 1:32, specifically 1:2 to 1:16, 1:4 to 1:16, 1:4 to 1:14, 1:6 to 1:14, more specifically 1:8 to 1:12, further more specifically 1:10. The amount and composition of the yielded isomers may be different depending on the ratio.

The dilution ratios of the cis, trans, random and twist stereoisomers may be different depending on the total amount of the solvent used. The proportion of the trans isomer decreases at lower dilution ratio and increases at higher dilution ratio. Also, the yield of total isomers may decrease as the dilution ratio increases.

In consideration of this, the monomer composition may be diluted to include the hydroxy-substituted cyclic siloxane at a ratio of 0.01-0.1 g based on 1 ml of the THF in the solvent in order to isolate the desired stereoisomers. The dilution ratio may be controlled by maintaining the amount of the stereoisomers constant and increasing the total solvent amount.

In an embodiment, the temperature of the monomer composition is not particularly limited as long as effective isolation of the isomers is possible without freezing of the solvent. The temperature may be specifically −15 to 25° C., more specifically 0-25° C. Although cyclohexane freezes at about 6° C., the freezing point of the mixture solvent may vary depending on the mixing ratio of THF. The mixture solvent of THF and cyclohexane with the afore-described ratio is capable of isolating the cyclic siloxane stereoisomers with desired ratios without freezing at 0-4° C. or room temperature condition. Above 25° C., deformation of cyclic siloxane may occur. And, below −15° C., the isomers cannot be isolated due to freezing.

The cis, trans, random and twist stereoisomers may be isolated effectively at desired ratios by controlling the kind of solvents, mixing ratios of the solvent in the mixture solvent, total amount of the solvent and temperature condition, as described above. And, the branch-type silsesquioxane polymer may be prepared by performing polymerization using the monomer composition for polymerizing a branch-type silsesquioxane polymer comprising the same.

In an embodiment, the molecular weight of the branch-type silsesquioxane polymer may be controlled by varying polymerization conditions depending on the ratios of the cis, trans, random and twist stereoisomers. The branch-type silsesquioxane polymer may have a weight average molecular weight of, for example, 5,000-1,500,000, specifically 60,000, 55,000 or 140,000.

The present disclosure also provides a method for preparing the branch-type silsesquioxane polymer, comprising: controlling the ratios of cis, trans, random and twist stereoisomers of hydroxy-substituted cyclic siloxane; and polymerizing the hydroxy-substituted cyclic siloxane with the cis, trans, random and twist stereoisomers at the controlled ratios as monomer in a solvent in the presence of a catalyst.

In an embodiment, the ratios of the stereoisomers may be controlled by changing the mixing ratio of a solvent in which the hydroxy-substituted cyclic siloxane is dissolved.

The solvent may be the same as the solvent included in the above-described monomer composition. For example, a mixture solvent of THF and cyclohexane may be used.

The mixture solvent may comprise THF and cyclohexane at a ratio of, for example, 1:1 to 1:32, specifically 1:2 to 1:16, 1:4 to 1:16, 1:4 to 1:14, 1:6 to 1:14, more specifically 1:8 to 1:12, further more specifically 1:10.

Although cyclohexane freezes at about 6° C., the freezing point of the mixture solvent may vary depending on the mixing ratio of THF. The mixture solvent of THF and cyclohexane with the afore-described ratio is capable of isolating the cyclic siloxane stereoisomers with desired ratios without freezing at 0-4° C. or room temperature condition. Above 25° C., deformation of cyclic siloxane may occur. And, below −15° C., the isomers cannot be isolated due to freezing.

In another embodiment, the ratios of the stereoisomers may be controlled by increasing the dilution ratio of the hydroxy-substituted cyclic siloxane in the solvent. The dilution ratio may be different depending on the total solvent amount.

In another embodiment, the solvent may be added to the hydroxy-substituted cyclic siloxane in a ratio of 0.01-0.1 g of the hydroxy-substituted cyclic siloxane based on 1 ml of the THF in the solvent in order to solate the desired stereoisomers. The dilution ratio may be controlled by maintaining the amount of the stereoisomers constant and increasing the total solvent amount.

The ratios of the cis, trans, random and twist stereoisomers may be controlled by controlling the kind of solvents, mixing ratios of the solvent in the mixture solvent, total amount of the solvent and temperature condition.

In an embodiment, the cis, trans, random and twist stereoisomers with controlled ratios may be polymerized as monomer in a solvent, e.g., toluene, hexane, methylene chloride, chloroform, THF, cyclohexane or a mixture thereof, in the presence of a catalyst such as $K_2CO_3$.

The present disclosure further provides a low dielectric material comprising the branch-type silsesquioxane polymer.

The branch-type silsesquioxane polymer polymerized from the cis, trans, random and twist stereoisomers with controlled ratios as monomer exhibit low dielectric property and improved thermal resistance due to good regularity. Accordingly, the branch-type silsesquioxane polymer of the present disclosure is an appropriate low dielectric material.

The examples and experiments will now be described. The following examples and experiments are for illustrative purposes only and not intended to limit the scope of this disclosure.

EXAMPLE 1

Identification of Isomer Composition and $^1$H NMR Peaks 2,4,6,8-Tetrahydroxytetramethylcyclosiloxane was prepared by completely substituting four isomers of cyclic siloxane. Isomer composition and $^1$H NMR peaks were identified.

Figure 2:
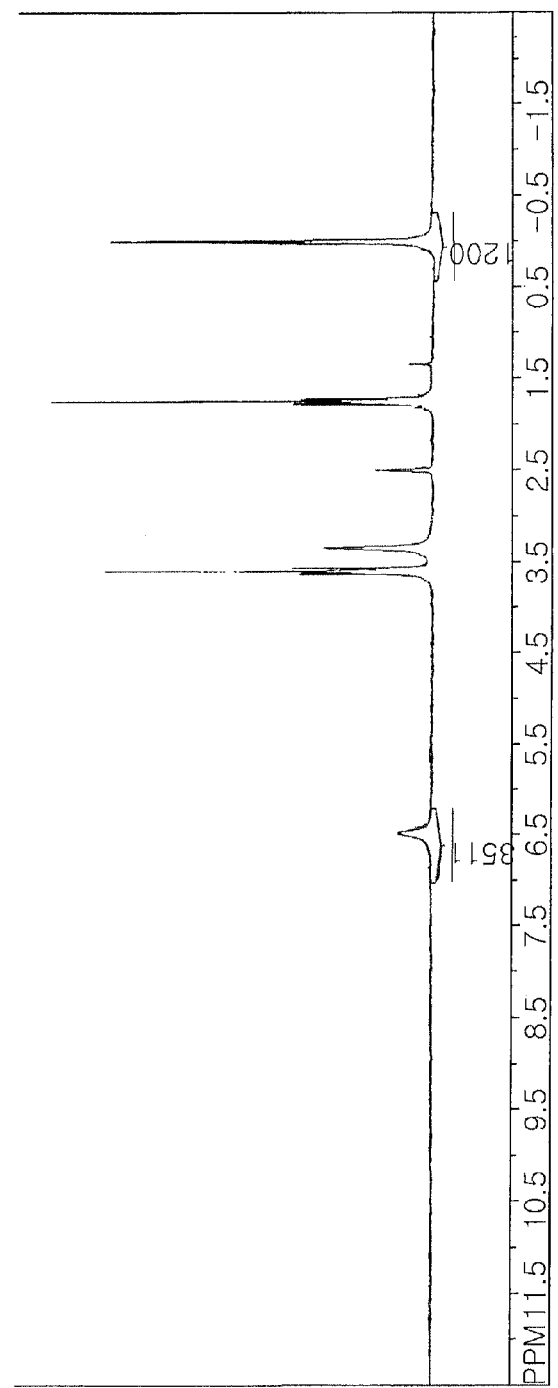
FIG. 2 shows a $^1$H NMR spectrum of 2,4,6,8-tetrahydroxytetramethylcyclosiloxane.
Figure 3:
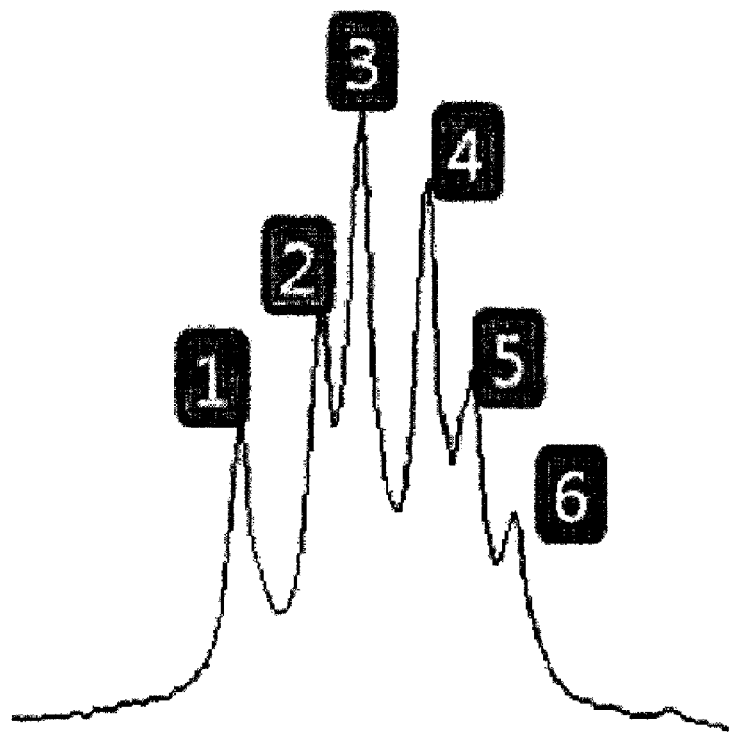
FIG. 3 shows peak positions in a $^1$H NMR spectrum for the four isolated structural isomers.

1H NMR peaks were given in Table 1, and the result of identifying the 1H NMR peaks is shown in FIGS. 2 and 3. 1H NMR peak positions and composition of each isomer are shown in Table 2. The peaks #1, 4 and 5 come from one random isomer.

TABLE 1

| peak # | freq. (Hz) | freq. (ppm) | intensity | intensity (absolute) |
|---|---|---|---|---|
| 1 | 7.619 | 0.0381 | 0.386548 | 83.499000 |
| 2 | 4.563 | 0.0228 | 0.567404 | 122.566000 |
| 3 | 3.080 | 0.0154 | 0.803682 | 173.605000 |
| 4 | 0.536 | 0.0027 | 0.734816 | 158.729000 |
| 5 | −1.198 | −0.0060 | 0.498394 | 107.659000 |
| 6 | −2.825 | −0.0141 | 0.295368 | 63.803000 |

TABLE 2

| Peak # | Isomer | Peak area |
|---|---|---|
| 6 | Cis | 5.28 |
| 5 | Random | 31.79 |
| 4 | Random | 16.33 |
| 3 | Trans | 17.01 |
| 2 | Twist | 18.44 |
| 1 | Random | 11.16 |

EXAMPLE 2

Establishment of Conditions for Isomer Isolation

The cyclic siloxane monomer (0.051~1.08 g) was prepared into 0.085 g/mL concentration in tetrahydrofuran (THF). The monomer solution was added to various solvents in varying amounts under various conditions described in Tables 3-6.

Figure 4:
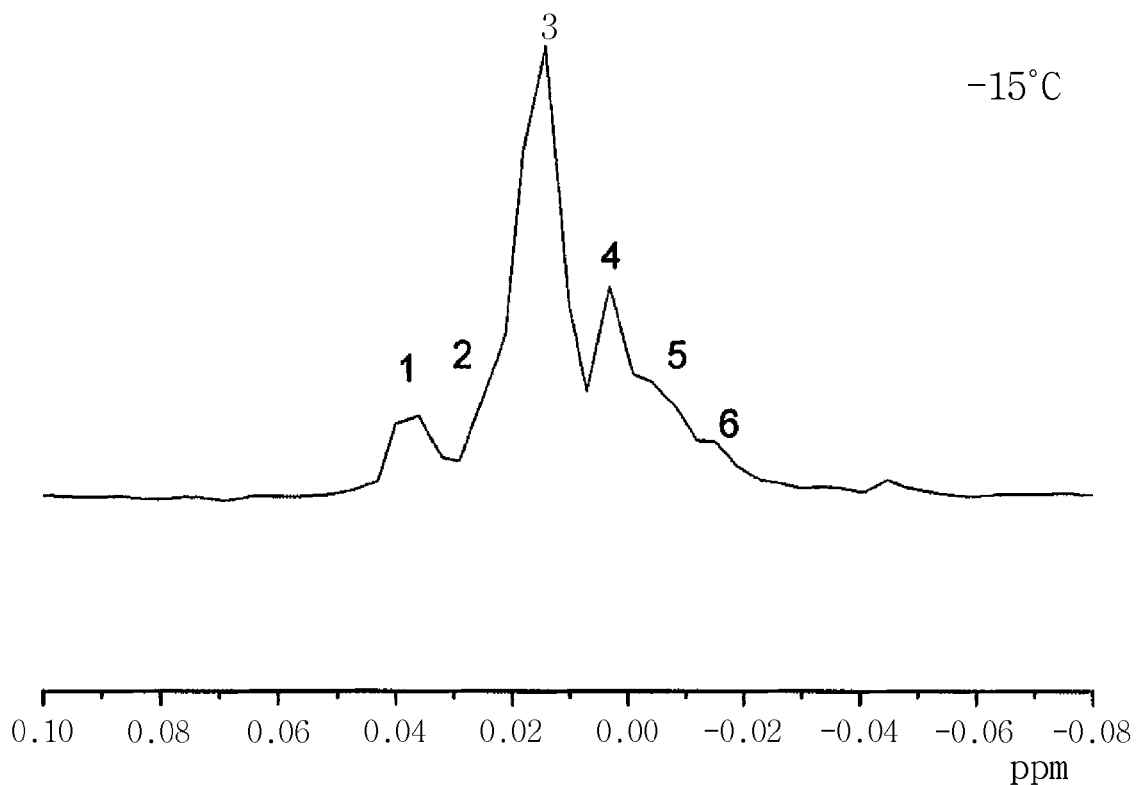
FIGS. 4-6 show the effect of temperature on isomer isolation analyzed through $^1$H NMR spectroscopy.
Figure 5:
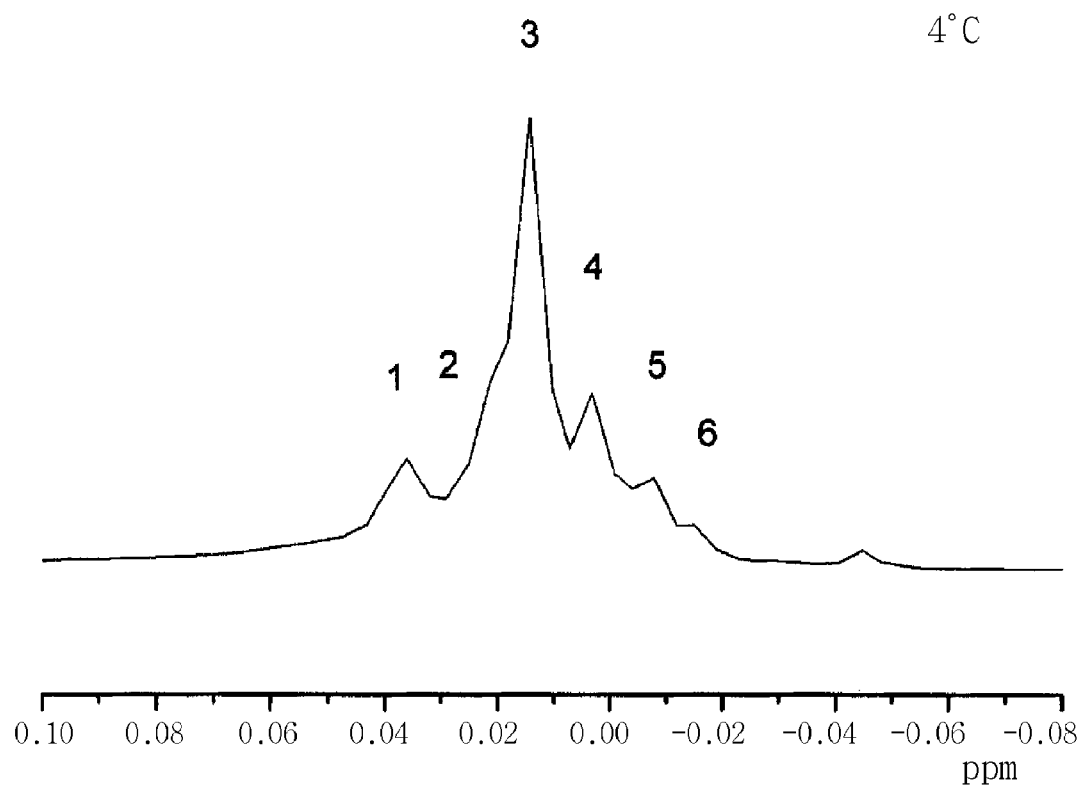
Figure 6:
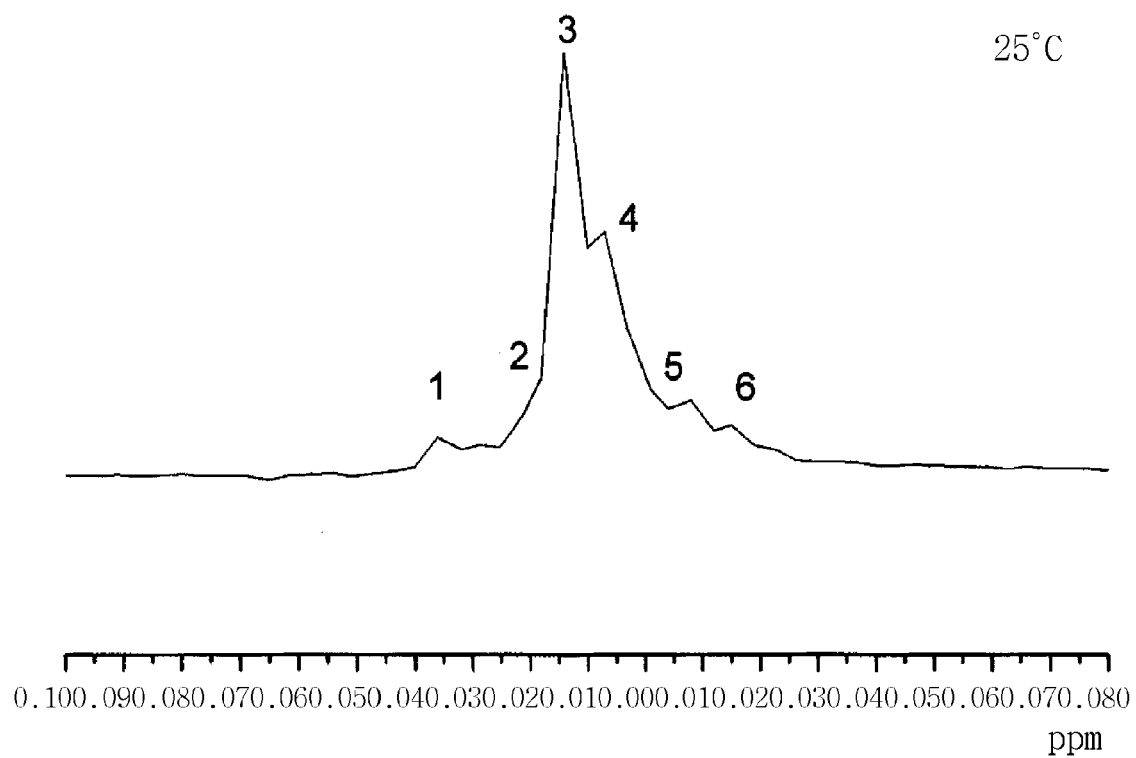

First, the effect of temperature on isomer isolation when 56 mL (total solvent amount) of 1:8 THF/cyclohexane was used was analyzed by $^1$H NMR spectroscopy. The result is shown in FIGS. 4-6. Details are given in Table 3.

TABLE 3

| | THF/Cyclohexane | | |
|---|---|---|---|
| | 1/8 Freezer (−15° C.) | 1/8_ICE (4° C.) | 1/8_RT (25° C.) |
| Total solvent amount | 56 | 56 | 56 |
| Cis | 6.12 | 3.68 | 5.27 |
| Random | 17.19 | 13.28 | 7.91 |
| Random | 14.78 | 13.6 | 27.7 |
| Trans | 34.97 | 34.63 | 47.78 |
| Twist | 19.01 | 26.5 | 6.74 |
| Random | 7.93 | 8.31 | 4.6 |

Figure 7:
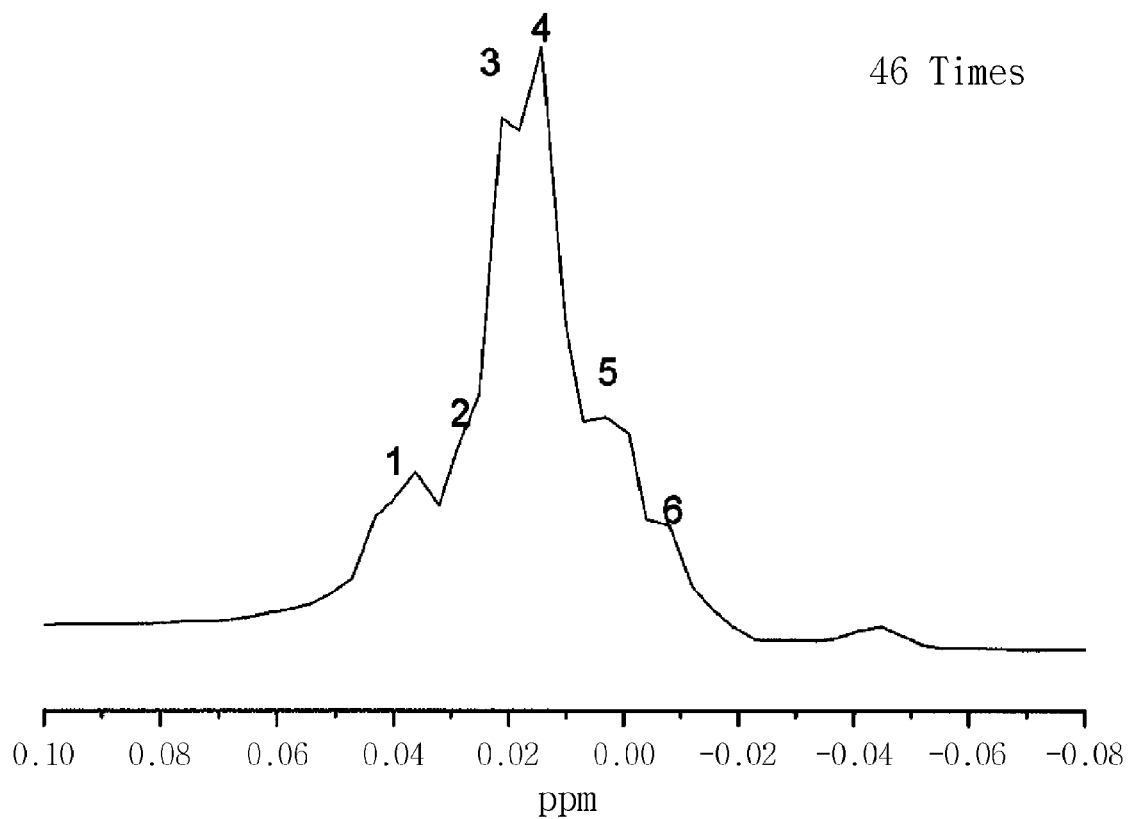
FIG. 7-9 show the effect of total solvent amount on isomer isolation analyzed through $^1$H NMR spectroscopy.
Figure 8:
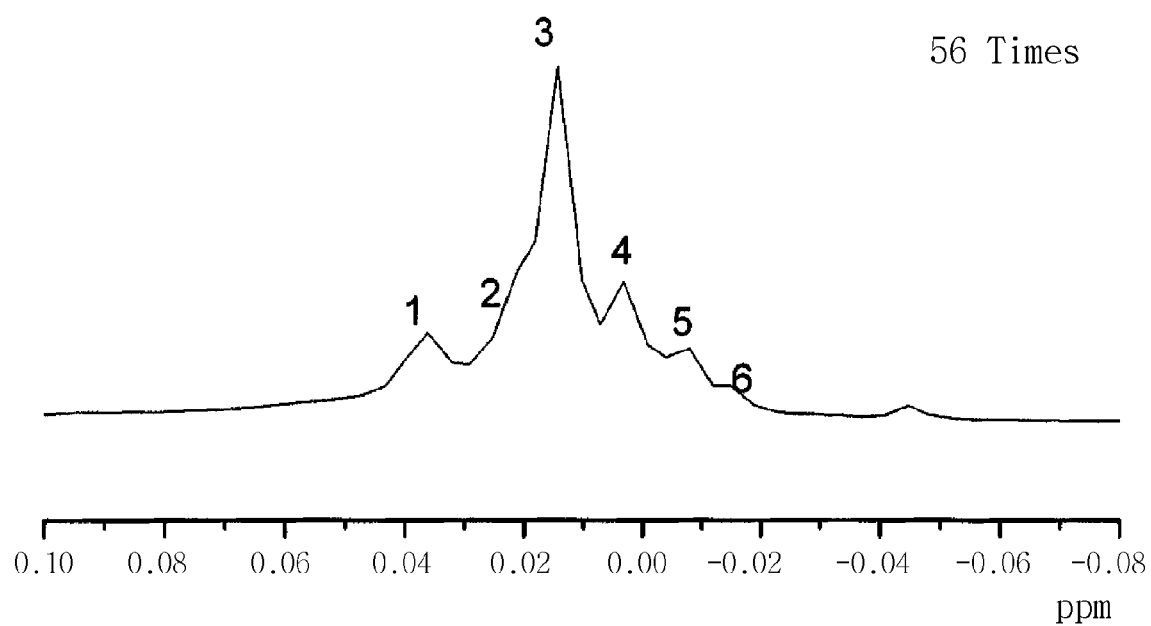
Figure 9:
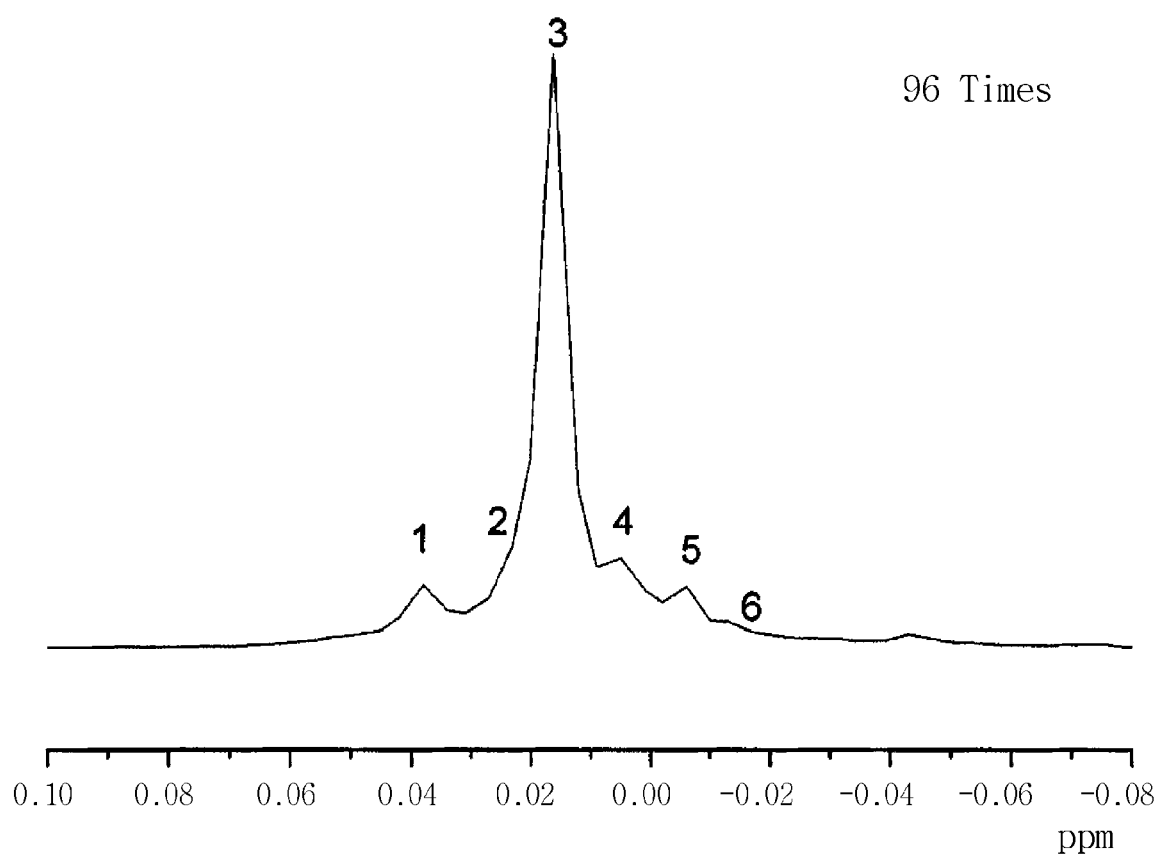

The effect of total solvent amount on isomer isolation when 1:8 THF/cyclohexane was used at cooling (4° C.) condition was analyzed by 1H NMR spectroscopy. The result is shown in FIGS. 7-9. Details are given in Table 4.

TABLE 4

| | THF/Cyclohexane | | | | |
|---|---|---|---|---|---|
| | 1/8_ICE | 1/8_ICE | 1/8_ICE | 1/8_ICE | 1/8_ICE |
| Total solvent amount | 46 | 56 | 70 | 84 | 98 |
| Cis | 1.98 | 4.29 | 3.88 | 8.26 | 2.5 |
| Random | 6.56 | 8.38 | 8.21 | 9.3 | 5.39 |
| Random | 19.67 | 16.82 | 19.96 | 15.58 | 12.16 |
| Trans | 33.2 | 39.61 | 40.05 | 38.19 | 54.06 |
| Twist | 24.67 | 18.08 | 16.42 | 20.78 | 18.8 |
| Random | 13.92 | 12.82 | 11.49 | 7.88 | 7.08 |

Figure 10:
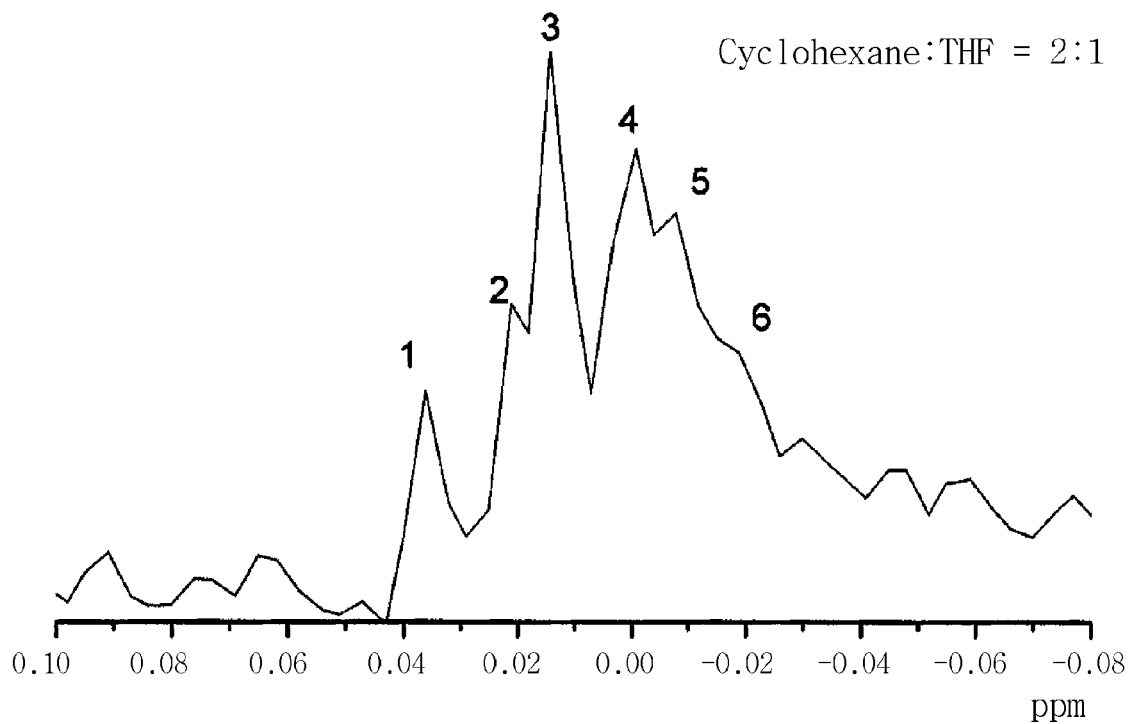
FIG. 10-12 show the effect of mixing ratio of a solvent on isomer isolation analyzed through $^1$H NMR spectroscopy.
Figure 11:
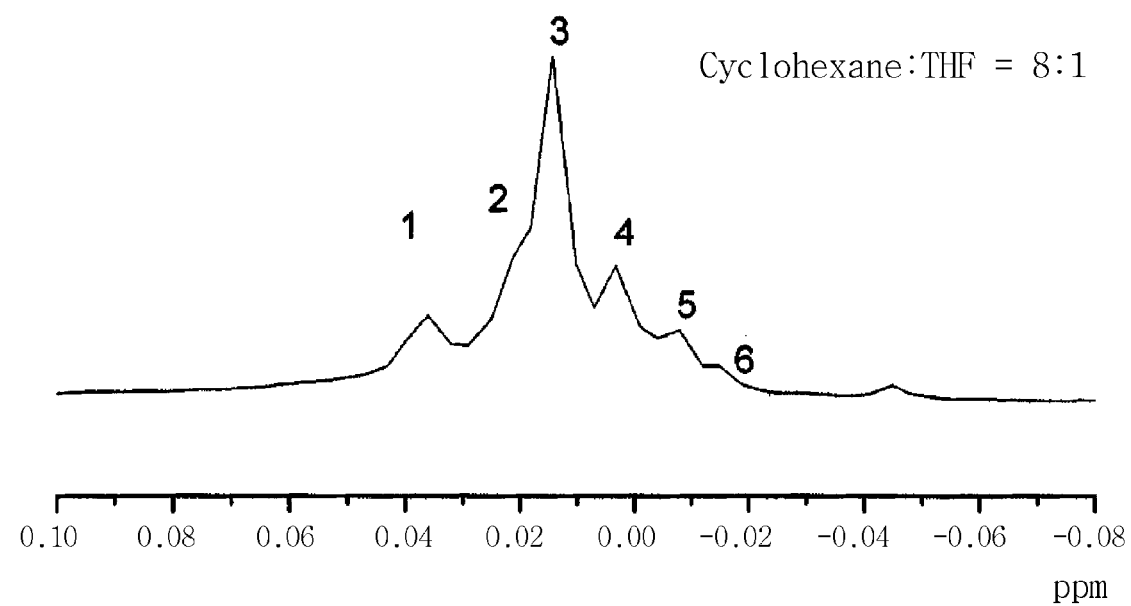
Figure 12:
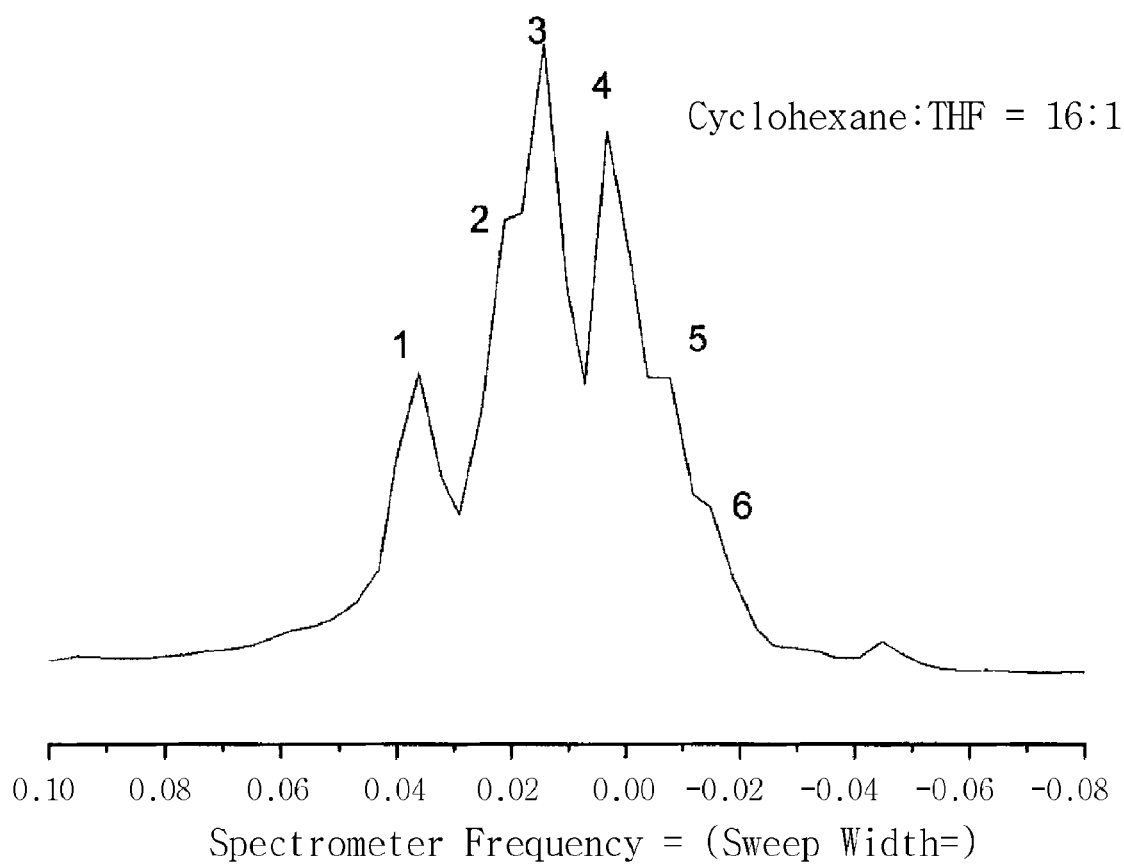
Figure 13:
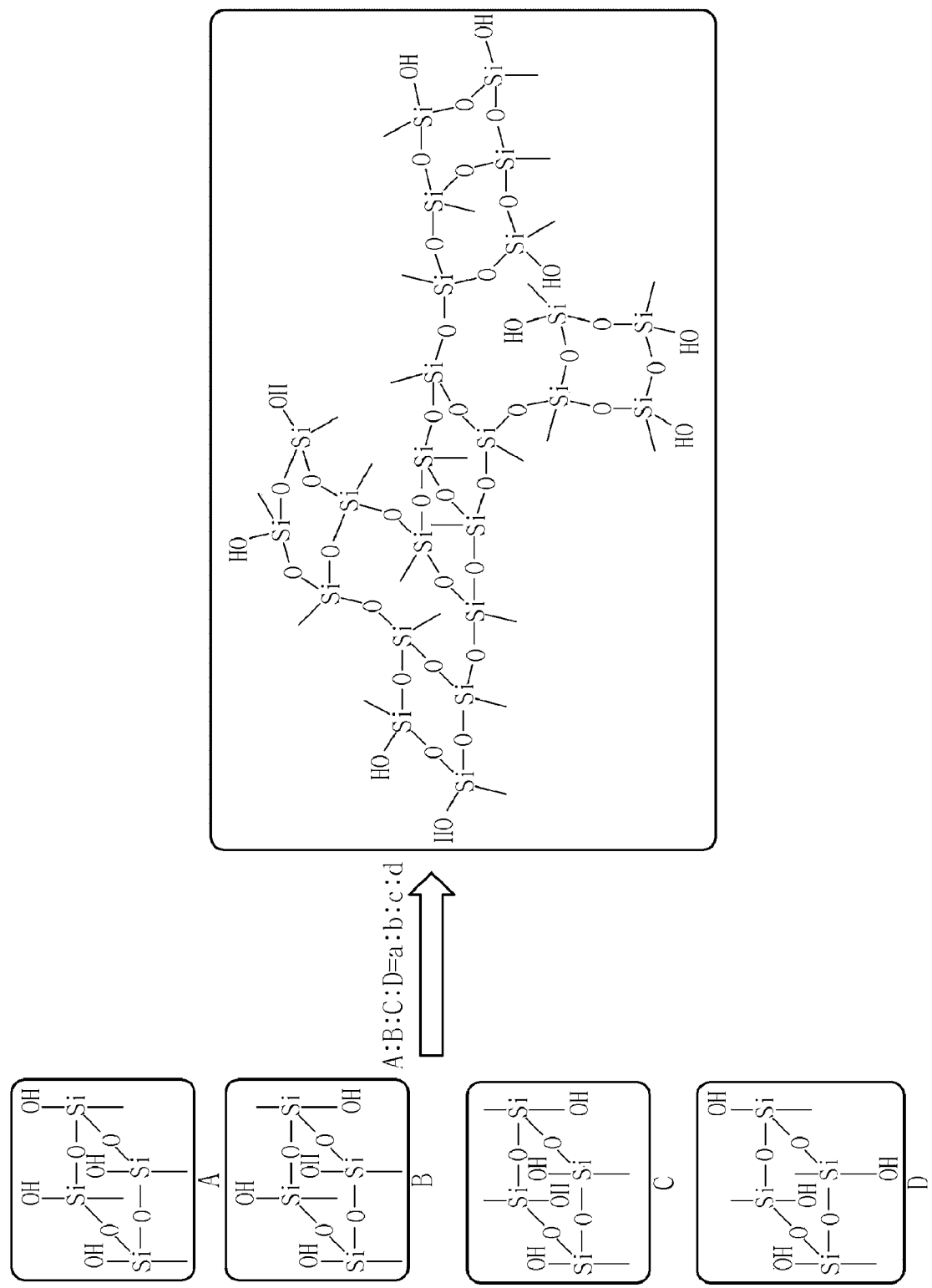
FIG. 13 shows a branch-type silsesquioxane polymer polymerized from the isolated isomers.

The effect of mixing ratio of a solvent on isomer isolation at cooling condition was analyzed by $^1$H NMR spectroscopy. The result is shown in FIGS. 10-12. Details are given in Tables 5 and 6.

TABLE 5

| | THF/Cyclohexane | | | | |
|---|---|---|---|---|---|
| | 1/2_ICE | 1/4_ICE | 1/6_ICE | 1/8_ICE | 1/8.5_ICE |
| Total solvent amount | 56 | 56 | 56 | 56 | 56 |
| Cis | 23.77 | 8.52 | 11.19 | 4.29 | 3.2 |
| Random | 18.94 | 13.17 | 11.39 | 8.38 | 7.31 |
| Random | 24.06 | 20.96 | 23.98 | 16.82 | 21.71 |
| Trans | 18.07 | 26.45 | 36.91 | 39.61 | 36.46 |
| Twist | 10.4 | 19.4 | 8.2 | 18.08 | 19.45 |
| Random | 4.76 | 11.49 | 8.32 | 12.82 | 11.87 |

TABLE 6

| 1/9_ICE | 1/9.5_ICE | 1/10_ICE | 1/12_ICE | 1/14_ICE | 1/16_ICE | 1/32_ICE |
|---|---|---|---|---|---|---|
| 56 | 56 | 56 | 56 | 56 | 56 | 56 |
| 7.7 | 3.98 | 7.36 | 5.31 | 7.98 | 7.06 | 6.03 |
| 11.33 | 9.94 | 15.33 | 10.98 | 15.48 | 13.52 | 11.56 |
| 22.17 | 23.79 | 22.51 | 30.62 | 19.54 | 20.83 | 23.23 |
| 36.71 | 33.3 | 25.26 | 24.43 | 37.42 | 29.3 | 25.26 |
| 13.41 | 16.73 | 12.21 | 18.06 | 8.58 | 15.99 | 23.09 |
| 8.67 | 12.26 | 17.33 | 10.61 | 11.01 | 13.31 | 10.82 |

EXAMPLE 3

Polymerization of Branch-Type Polymer Using Isolated Isomers

Polymers of different structures were polymerized by controlling the fractions of the structural isomers.

Polymerization was performed using isomers with different trans isomer ratios as shown in Table 7. Table 7 shows polymerization conditions and molecular weight of polymers depending on isomer ratios.

TABLE 7

| Condition | Abbreviation | Trans | Others | Mw |
|---|---|---|---|---|
| 1 | PB35ppt | 35 | 55 | 60,000 |
| 2 | PB55ppt | 55 | 35 | 55,000 |
| 3 | PB85ppt | 85 | 15 | 1,410,000 |

The isomer isolation condition for Pb35ppt was 1:8 THF/cyclohexane, 56 mL of total solvent amount and cooling condition. The isomer isolation condition for Pb55ppt was 1:8 THF/cyclohexane, 98 mL of total solvent and cooling condition. And, the isomer isolation condition for PB85ppt was 1:8 THF/cyclohexane, 98 mL of total solvent amount and cooling condition. The obtained powder was diluted and polymerized under the same condition.

Polymerization was carried out using 0.1 g/mL THF and 0.5 wt % $K_2CO_3$. The molecular weight was controlled through reaction time. The reaction was performed for 2 days under Condition 1 in Table 7, for 3 days under Condition 2, and for 4 days under Condition 3.

Figure 14:
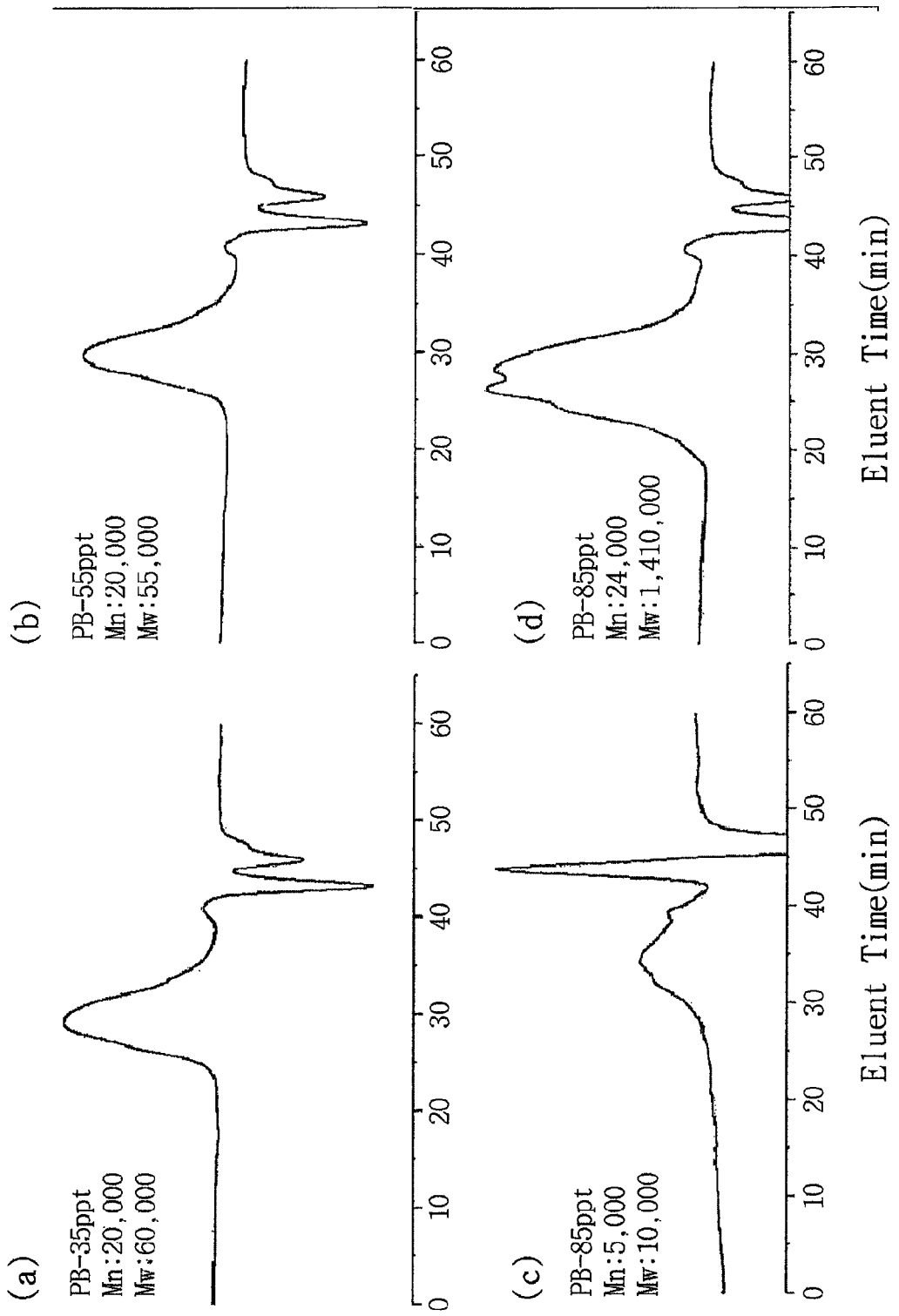
FIG. 14 shows molecular weight distribution of the branch-type silsesquioxane polymer depending on the isomer ratios.
Figure 15:
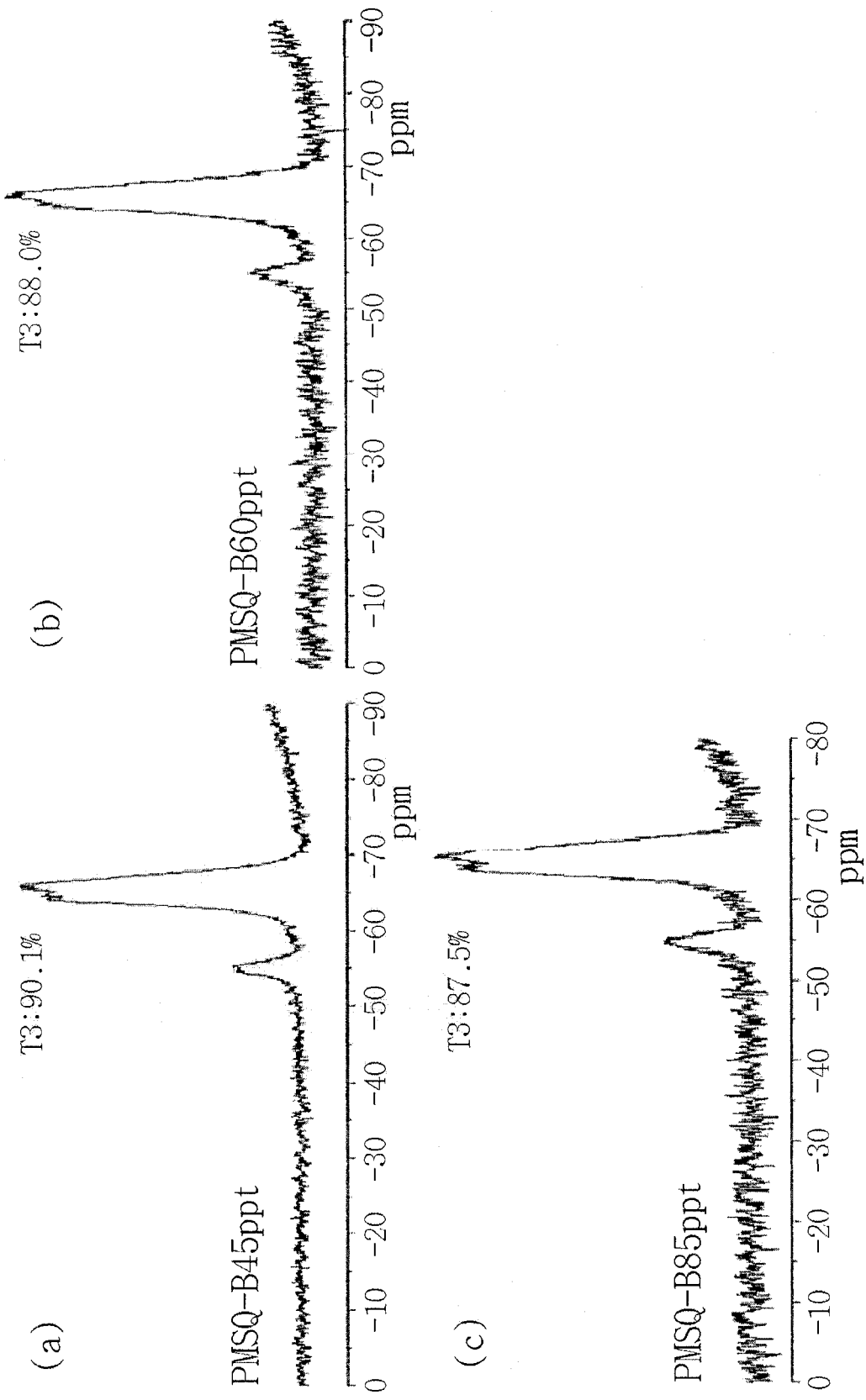
FIG. 15 shows $^{29}$Si NMR spectra of the branch-type silsesquioxane polymer depending on the isomer ratios.

The weight average molecular weight of the resulting polymers was 60,000 under Condition 1, 55,000 under Condition 2, and 1,400,000 under Condition 3 (FIG. 14). Molecular structure of the polymerized branch-type PMSQ polymers was identified by 29Si NMR spectroscopy (FIG. 15). 35% trans PMSQ (PB35ppt) exhibited about 90% T3 structure. PB55ppt and PB85ppt exhibited 88% T3 structure. The high T3 structure suggests that the polymerized polymers are not simply radial polymers.

Figure 16:
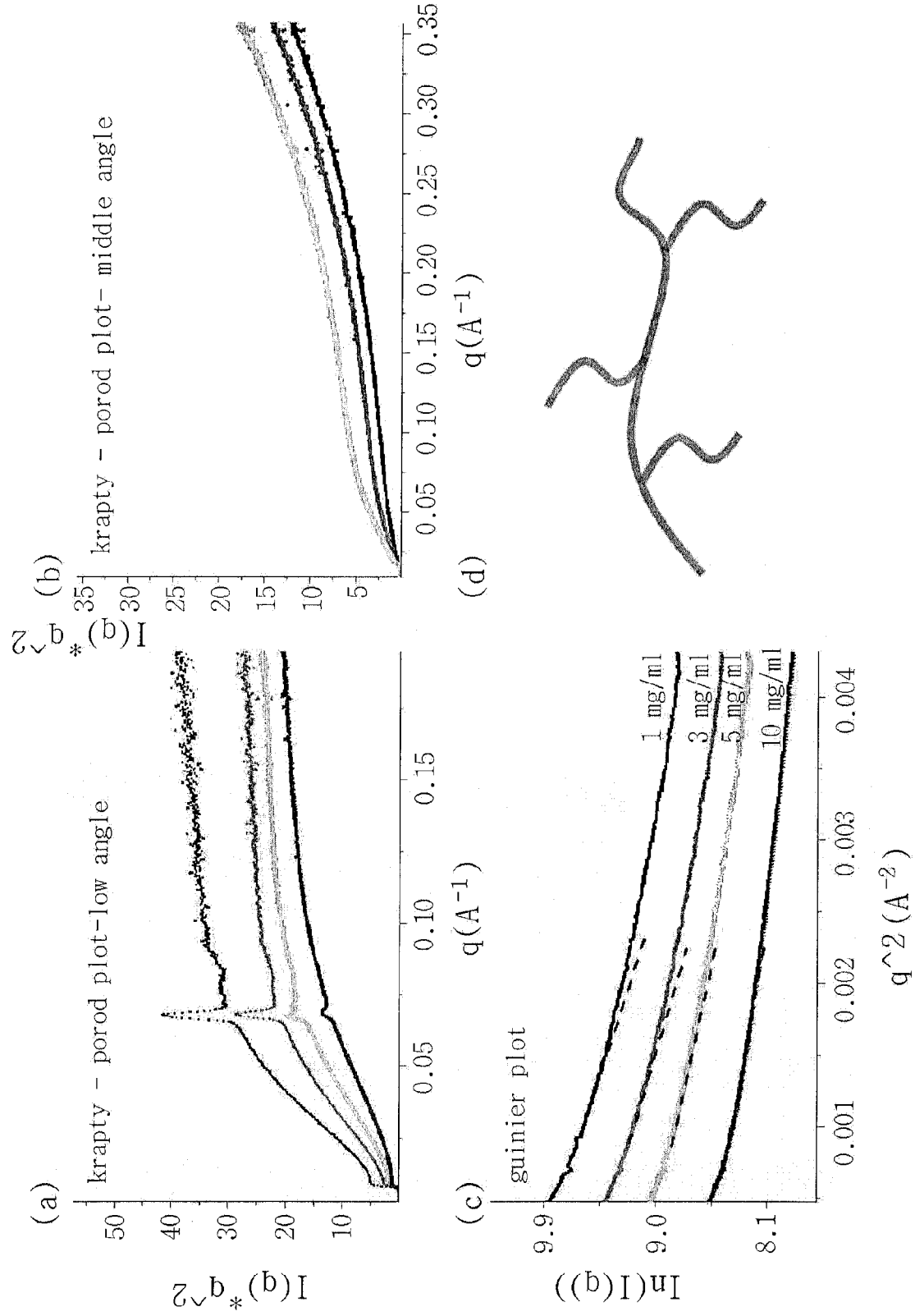
FIG. 16 shows a result of small-angle X-ray scattering (SAXS) molecular structure analysis of the branch-type silsesquioxane polymer depending on the isomer ratios.

The shape of the branch-type polymers was analyzed by small-angle X-ray scattering (SAXS). The size and shape of PB85ppt molecules were analyzed through Krafty-Porod plot and Guinier plot, in the 0.005-0.5 q ($Å^{-1}$) region. The result is shown in FIG. 16.

The effect of concentration on molecular size was investigated. The molecular size was larger at lower concentrations. Also, the persistence length increased at lower concentrations. This suggests that the degree of spreading of branches emanating from the backbone is affected by the concentrations. At higher concentrations, the molecular size is reduced and the persistence length also decreases since the branches cannot spread. At lower concentrations, the molecular size and the persistence length increase since the branches can spread freely. Thus, it is predicted that the branches emanate from the linear polymer backbone like a comb.

Figure 17:
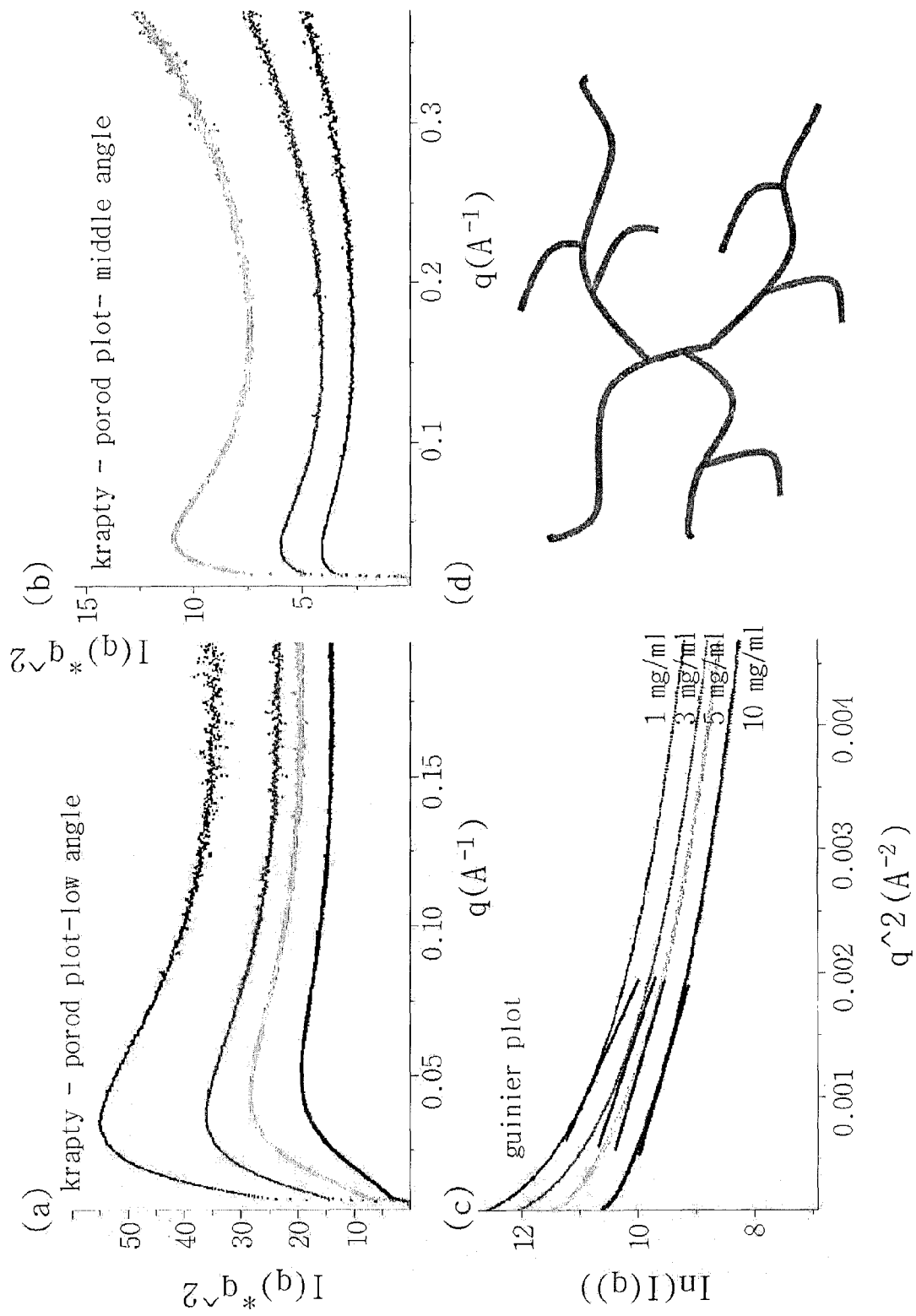
FIG. 17 shows a result of SAXS molecular structure analysis of the branch-type silsesquioxane polymer depending on the isomer ratios.

The size and shape of PB55ppt molecules were also analyzed through Krafty-Porod plot and Guinier plot, in the 0.005-0.5 q ($Å^{-1}$) region. The result is shown in FIG. 17. The effect of concentration on molecular size was investigated. The molecular size was larger at lower concentrations, but the persistence length did not change. This suggests that the degree of spreading of branches emanating from the backbone is affected by the concentrations. At higher concentrations, the molecular size is reduced since the branches cannot spread. In contrast, at lower concentrations, the molecular size increases since the branches can spread freely. The fact that the persistence length does not change suggests that the polymer is of hyperbranched type with the branch shape remaining unchanged.

Figure 18:
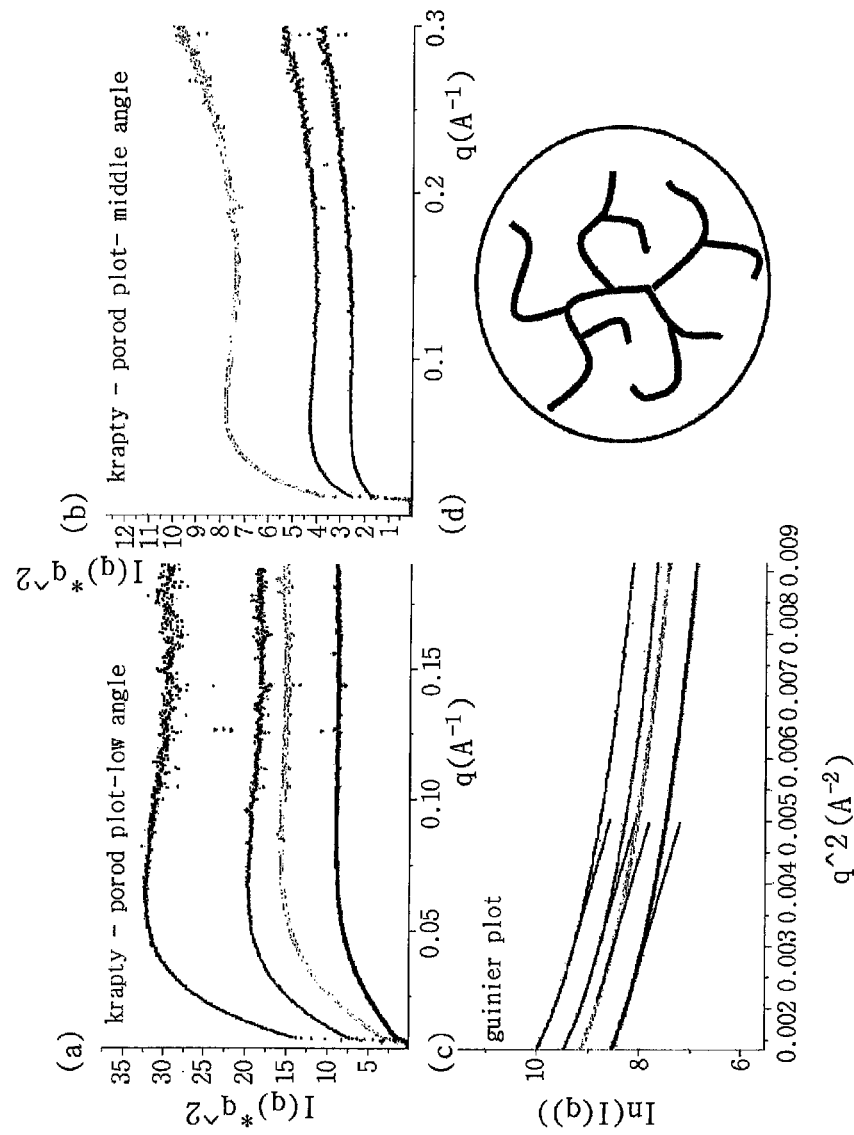
FIG. 18 shows a result of SAXS molecular structure analysis of the branch-type silsesquioxane polymer depending on the isomer ratios.

The size and shape of PB35ppt molecules were also analyzed. The result is shown in FIG. 18. Through the Guinier plot, it was confirmed that the polymer showed no change in molecular size depending on concentration. Also, through the Krafty-Porod plot, it was confirmed that the polymer showed no change in persistence length depending on concentration. Thus, it is predicted that the PB35ppt polymer is in spherical form rather than in branched form.

EXAMPLE 4

Thermal Resistance and Surface Modulus of Branch-Type Polymers

Figure 19:
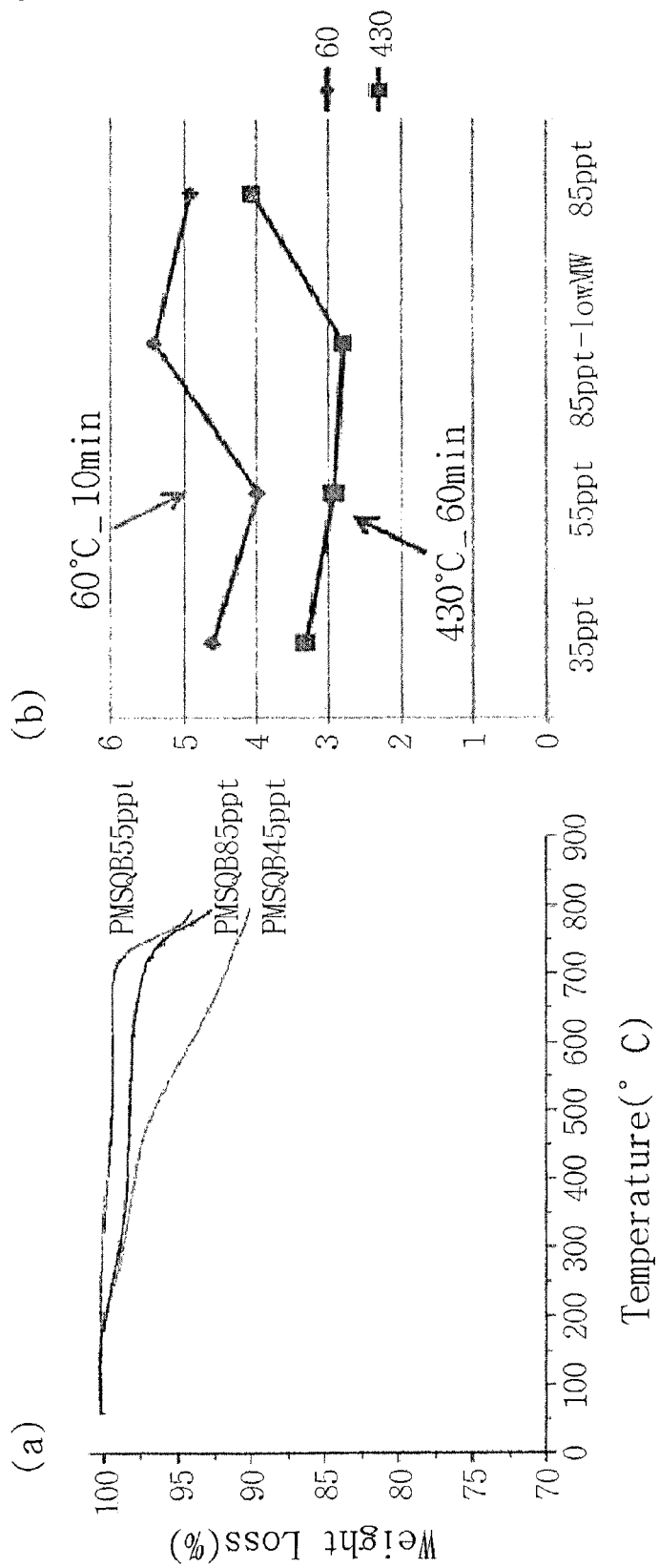
FIG. 19 shows a result of thermogravimetric analysis (TGA) and change in surface modulus before and after heat treatment of the branch-type silsesquioxane polymer.

Thermal stability and surface modulus of the polymerized PMSQs were investigated. The result is shown in FIG. 19. As seen from FIG. 19 (a), PB85ppt and PB50ppt showed good thermal stability up to 700° C. or higher. PB35ppt started to be decomposed at 450° C. like commonly known other PMSQs. This suggests that the branch-type polymers have increased thermal resistance due to improved regularity, like ladder-type PMSQ polymers.

Surface modulus was measured after heat treatment at 430° C. for 2 hours. The result is shown in FIG. 19 (b). When the polymers were measured after drying at 60° C. for 10 minutes, the surface modulus of PB35ppt, PB55ppt and PB85ppt was 3.2 GPa, 2.9 GPa and 4.1 GPa, respectively. After the heat treatment, the surface modulus was decreased by about 10%. This suggest that the free volume in the matrix was increased due to the reaction between the terminal groups of the branch-type polymer.

EXAMPLE 5

Preparation of Low Dielectric Material

Figure 20:
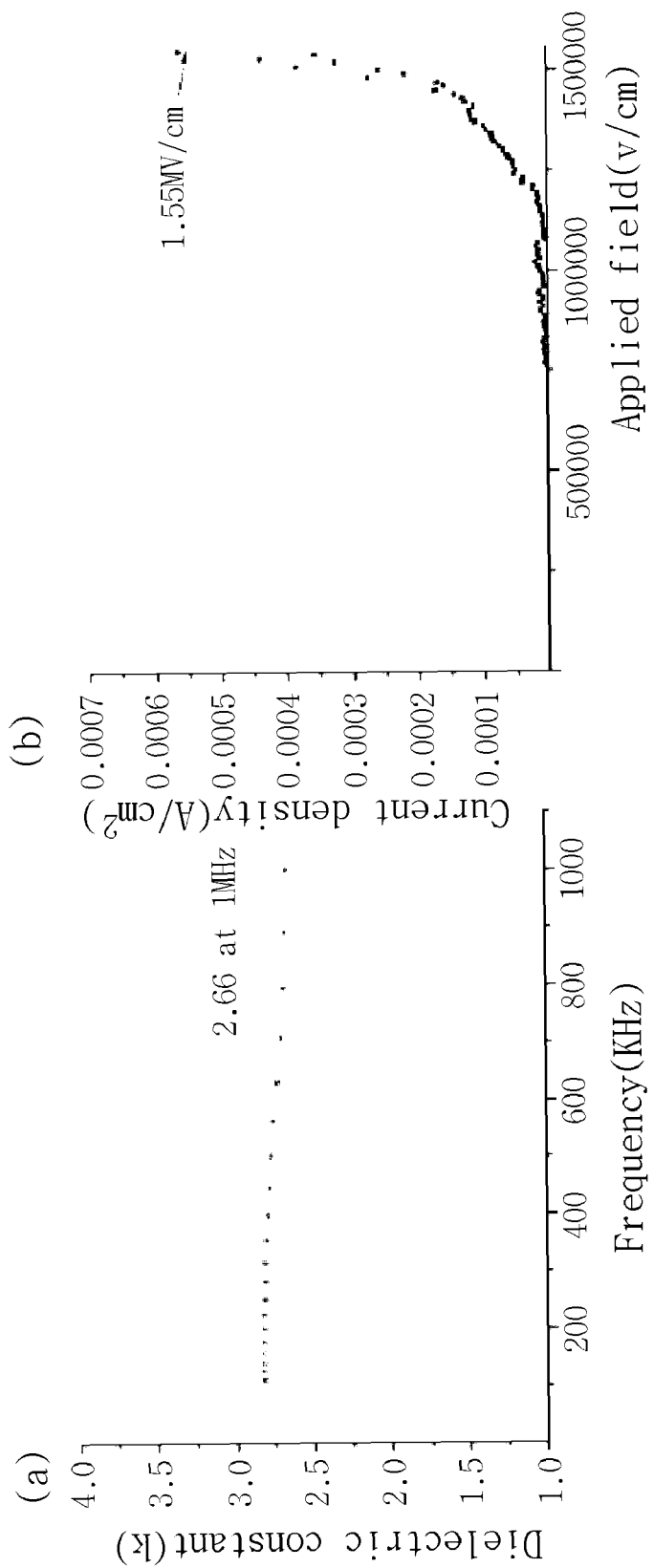
FIG. 20 shows a result of dielectric constant and breakdown voltage measurement after heat treatment of the branch-type silsesquioxane polymer.

Dielectric constant and breakdown voltage of PB55ppt, which exhibited the best coating property, were measured. The result is shown in FIG. 20. A low dielectric material was successfully prepared using the polymer matrix, with a dielectric constant of 2.66 and a breakdown voltage of 1.55 MV/cm.

While the exemplary embodiments have been shown and described, it will be understood by those skilled in the art that various changes in form and details may be made thereto without departing from the spirit and scope of this disclosure as defined by the appended claims.

In addition, many modifications can be made to adapt a particular situation or material to the teachings of this disclosure without departing from the essential scope thereof. Therefore, it is intended that this disclosure not be limited to the particular exemplary embodiments disclosed as the best mode contemplated for carrying out this disclosure, but that this disclosure will include all embodiments falling within the scope of the appended claims.

The invention claimed is:

1. A monomer composition for preparing a branch-type silsesquioxane polymer, comprising hydroxy-substituted cyclic siloxane in a solvent, wherein the hydroxy-substituted cyclic siloxane comprises stereoisomers of cyclic siloxane of cis, trans, random and twist structures at controlled ratios, wherein the ratio of the trans stereoisomer in the stereoisomers is 35-85%.

2. The monomer composition according to claim 1, wherein the solvent is one or more selected from a group consisting of toluene, hexane, methylene chloride, chloroform, tetrahydrofuran (THF), cyclohexane and a mixture thereof.

3. The monomer composition according to claim 1, wherein the solvent is a mixture solvent of THF and cyclohexane.

4. The monomer composition according to claim 3, wherein the mixture solvent comprises THF and cyclohexane at a ratio of 1:1 to 1:32.

5. The monomer composition according to claim 3, wherein the monomer composition comprises the hydroxy-substituted cyclic siloxane at a ratio of 0.01-0.1 g based on 1 ml of the THF in the solvent.

6. The monomer composition according to claim 1, wherein the temperature of the monomer composition is controlled at −15 to 25° C.

7. The monomer composition according to claim 1, wherein the temperature of the monomer composition is controlled at 0-4° C.

8. A method for synthesizing a branch silsesquioxane polymer obtained by polymerizing the monomer composition according to claim 1, comprising:
controlling ratios of cis, trans, random and twist stereoisomers of hydroxy-substituted cyclic siloxane, wherein the ratio of the trans stereoisomer in the stereoisomers is 35-85%; and
polymerizing the hydroxy-substituted cyclic siloxane with the cis, trans, random and twist stereoisomers at the controlled ratios in a solvent in the presence of a catalyst.

9. The method for synthesizing the branch-type silsesquioxane polymer according to claim 8, wherein said controlling the ratios of the cis, trans, random and twist stereoisomers comprises changing the mixing ratio of a solvent in which the hydroxy-substituted cyclic siloxane is dissolved.

10. The method for synthesizing the branch-type silsesquioxane polymer according to claim 8, wherein, in said controlling the ratios of the cis, trans, random and twist stereoisomers, a mixture solvent of tetrahydrofuran (THF) and cyclohexane is used.

11. The method for synthesizing the branch-type silsesquioxane polymer according to claim 10, wherein, in said controlling the ratios of the cis, trans, random and twist stereoisomers, a mixture solvent comprising THF and cyclohexane at a ratio of 1:1 to 1:32 is used.

12. The method for synthesizing the branch-type silsesquioxane polymer according to claim 10, wherein, in said controlling the ratios of the cis, trans, random and twist stereoisomers, the temperature of the solution of the hydroxy-substituted cyclic siloxane is controlled at −15 to 25° C.

13. The method for synthesizing the branch-type silsesquioxane polymer according to claim 12, wherein, in said controlling the ratios of the cis, trans, random and twist stereoisomers, the temperature of the solution of the hydroxy-substituted cyclic siloxane is controlled at 0-4° C.

14. The method for synthesizing the branch-type silsesquioxane polymer according to claim 10, wherein, said controlling the ratios of the cis, trans, random and twist stereoisomers comprises adding the solvent to the hydroxy-substituted cyclic siloxane in a ratio of 0.01-0.1 g of the hydroxy-substituted cyclic siloxane based on 1 ml of the THF in the solvent.

* * * * *